(12) United States Patent
Lawrence

(10) Patent No.: US 12,245,917 B2
(45) Date of Patent: Mar. 11, 2025

(54) EARPLUG

(71) Applicant: Triton Systems, Inc., Chelmsford, MA (US)

(72) Inventor: Tyson Lawrence, Cambridge, MA (US)

(73) Assignee: Triton Systems, Inc., Chelmsford, MA (US)

( * ) Notice: Subject to any disclaimer, the term of this patent is extended or adjusted under 35 U.S.C. 154(b) by 180 days.

(21) Appl. No.: 15/806,061

(22) Filed: Nov. 7, 2017

(65) Prior Publication Data

US 2018/0125717 A1    May 10, 2018

Related U.S. Application Data

(60) Provisional application No. 62/418,345, filed on Nov. 7, 2016.

(51) Int. Cl.
| | |
|---|---|
| *A61F 11/08* | (2006.01) |
| *A61F 11/12* | (2006.01) |
| *A61F 11/14* | (2006.01) |
| *B63C 11/06* | (2006.01) |
| *B63C 11/26* | (2006.01) |

(52) U.S. Cl.
CPC .............. *A61F 11/08* (2013.01); *A61F 11/12* (2013.01); *A61F 11/14* (2013.01); *B63C 11/06* (2013.01); *A61F 11/085* (2022.01); *B63C 11/26* (2013.01)

(58) Field of Classification Search
CPC ........ A61F 11/08; A61F 11/008; A61F 11/30; A61F 11/00–145; A61M 39/233; A61M 39/22; A61M 2039/064; A61H 2205/027; F16K 17/003; F16K 17/22; F16K 17/26; F16K 17/28; F16K 17/19; B63C 11/00; B63C 11/02; B63C 11/04; B63C 11/06; B63C 11/26; H04R 1/10–1016; H04R 1/1083–1091
USPC ......................................................... 128/868
See application file for complete search history.

(56) References Cited

U.S. PATENT DOCUMENTS

| | | | | |
|---|---|---|---|---|
| 2,458,884 | A | | 1/1949 | Volkmann |
| 2,619,960 | A | * | 12/1952 | Reynolds ................ A61F 11/08 128/868 |
| 3,730,181 | A | * | 5/1973 | Fling ...................... A61F 11/08 128/868 |
| 3,941,149 | A | * | 3/1976 | Mittleman .............. F16K 17/19 137/493.1 |
| 4,353,364 | A | * | 10/1982 | Woods .................... A61F 11/08 128/867 |
| 5,483,027 | A | | 1/1996 | Krause |
| 5,819,745 | A | | 10/1998 | Mobley et al. |
| 6,567,524 | B1 | * | 5/2003 | Svean .................... A61F 11/08 381/317 |
| 7,740,104 | B1 | * | 6/2010 | Parkins .................. A61F 11/08 181/129 |

(Continued)

OTHER PUBLICATIONS

International Search Report and Written Opinion for PCT/US2017/060445 dated Feb. 21, 2018.

*Primary Examiner* — Michelle J Lee
(74) *Attorney, Agent, or Firm* — Caldwell Intellectual Property Law

(57) ABSTRACT

Devices, apparatus, systems and methods to regulate pressure in earplug are disclosed. Some embodiments provide auditory attenuation and others may further include communications capability. The devices and apparatus are well-suited for use by divers and pilots in particular.

17 Claims, 9 Drawing Sheets

(56) References Cited

U.S. PATENT DOCUMENTS

| | | | |
|---|---|---|---|
| 8,631,801 B2 | 1/2014 | Keady | |
| 2006/0042866 A1 | 3/2006 | Widmer et al. | |
| 2010/0002897 A1* | 1/2010 | Keady | H04R 25/554 |
| | | | 381/328 |
| 2010/0071708 A1* | 3/2010 | Lenhardt | A61F 11/08 |
| | | | 128/868 |
| 2011/0301572 A1* | 12/2011 | Vlodaver | A61F 11/00 |
| | | | 604/246 |
| 2013/0061376 A1* | 3/2013 | Halfaker | A42B 3/166 |
| | | | 2/414 |
| 2016/0022498 A1* | 1/2016 | Dittrich | A61F 11/08 |
| | | | 128/864 |
| 2016/0151206 A1* | 6/2016 | George | A61F 11/12 |
| | | | 128/866 |
| 2018/0104391 A1* | 4/2018 | Luxon | A61M 1/73 |
| 2019/0038393 A1* | 2/2019 | Banco | A61F 2/966 |

* cited by examiner

EARPLUG

CROSS-REFERENCE TO RELATED APPLICATIONS

The current application claims the benefit of U.S. Provisional Application No. 62/418,345, entitled EARPLUG, filed Nov. 7, 2016, which is hereby incorporated by reference in its entirety.

GOVERNMENT INTERESTS

This invention was made with Government support under Contract No. N00014-12-M-0342 awarded by the Department of the Navy. The United States Government has certain rights in this invention.

FIELD

This disclosure relates generally to devices, apparatus, systems and methods to regulate pressure in earplug. Some embodiments provide auditory attenuation and other may further include communications capability.

BACKGROUND

Earplugs are devices that are designed to be inserted in the ear canal and to protect the user's ears from different elements such as noise, water, wind, gas, dust, or other materials that could enter the ear canal. Earplugs can be coupled with other devices and be used for other applications such as, for example, enhance the hearing ability of the user and transmit information to the user. When installed, the earplug creates a barrier between the ear canal and the environment, and a difference of pressure can arise.

Conventional earplugs, though long used to provide auditory attenuation and protection in high decibel or otherwise harmful environments, present a number of problems. For example, conventional ear plugs typically offer fixed sound attenuation and must be completely removed from the canal for the user to hear. Moreover, earplugs that are capable of attenuating sound by 20-30 dB cannot be worn while, for example, diving or operating an airplane because of pressure changes. To overcome the change of pressure, vented earplugs can be used. However, vented earplugs provide significantly less attenuation and are prone to clogging.

Accordingly, there remains a critical need for a better-designed pressure equalizing earplugs.

SUMMARY OF THE INVENTION

Some embodiments provide a pressure-regulating earplug comprising an earplug body having an external surface adapted for sealingly engaging an ear canal and defining an exterior bore and an interior bore connected via a conduit such that the conduit is in fluid communication with an external atmosphere and the ear canal; a pressure regulator affixed to the earplug body and adapted for selectively opening in response to increase pressure differential to allow release of pressure in either direction to equilibrate pressure between the external atmosphere and the ear canal.

In some embodiments, the pressure regulator is a passive, two-way valve.

In some embodiments, the passive, two-way valve opening threshold is at a pressure differential of at about 0.1 psi or higher to allow pressure to flow from high to low.

In some embodiments, the passive, two-way valve opening threshold is a pressure differential of less than about 0.5 psi to allow pressure to flow from high to low.

In some embodiments, the passive, two-way valve opening threshold is a pressure differential from about 0.3 psi to about 1.5 psi In some embodiments, the pressure regulator is selected from an umbrella valve assembly, a duckbill valve assembly, a belleville valve assembly, a valveball assembly, a cross-split valve assembly, a dome valve assembly, or any combination thereof In some embodiments, the pressure regulator is selected from an umbrella valve assembly and a duckbill valve assembly or a combination thereof.

In some embodiments, the pressure regulator is a cross-split valve assembly.

In some embodiments, the pressure regulator comprises any of silicon, fluorosilicone, fluoro elastomer, perfluoroelastomer, nitrile, ethylene propylene, natural rubber, butyl, polyisoprene, or any combination thereof In some embodiments, the earplug body comprises a flanged earplug.

In some embodiments, the flanged ear plug is a single, a dual or triple flanged earplug.

In some embodiments, the flanged earplug is an elastomer earplug, foam earplug, silicon earplug, or any combination thereof.

Some embodiments further comprise a communication system.

Some embodiments provide a pressure-regulating earplug comprising an earplug body having an external surface adapted for sealingly engaging an ear canal and defining an exterior bore and an interior bore connected via a conduit such that the conduit is in fluid communication with an external atmosphere and the ear canal, and further comprising at least one additional conduit; a pressure regulator affixed to the earplug body and adapted for selectively opening in response to increase pressure differential to allow release of pressure in either direction to equilibrate pressure between the external atmosphere and the ear canal; and wherein the at least one additional conduit to house additional components.

In some embodiments, the additional components are selected from electrical components, communications system components, wiring, or combinations thereof In some embodiments, the at least one additional conduit is sealed against the external atmosphere.

In some embodiments, the external atmosphere is water, and the additional conduit is sealed against water influx.

Some embodiments provide pressure-regulating earplug system comprising a diver's helmet; ear muffs adapted to envelop the user's entire ear; pressure-regulating earplug comprising an earplug body having an external surface adapted for sealingly engaging an ear canal and defining an exterior bore and an interior bore connected via a conduit such that the conduit is in fluid communication with an external atmosphere and the ear canal, and a pressure regulator affixed to the earplug body and adapted for selectively opening in response to increase pressure differential to allow release of pressure in either direction to equilibrate pressure between the external atmosphere and the ear canal.

Other embodiments will be apparent in light of the description and drawings herein. This disclosure is meant to be illustrative and is not intended to be limited to the embodiments disclosed.

BRIEF DESCRIPTION OF THE DRAWINGS

Exemplary embodiments of the present invention will become more fully understood from the detailed description and the accompanying drawings, wherein.

DETAILED DESCRIPTION

Figure 1:
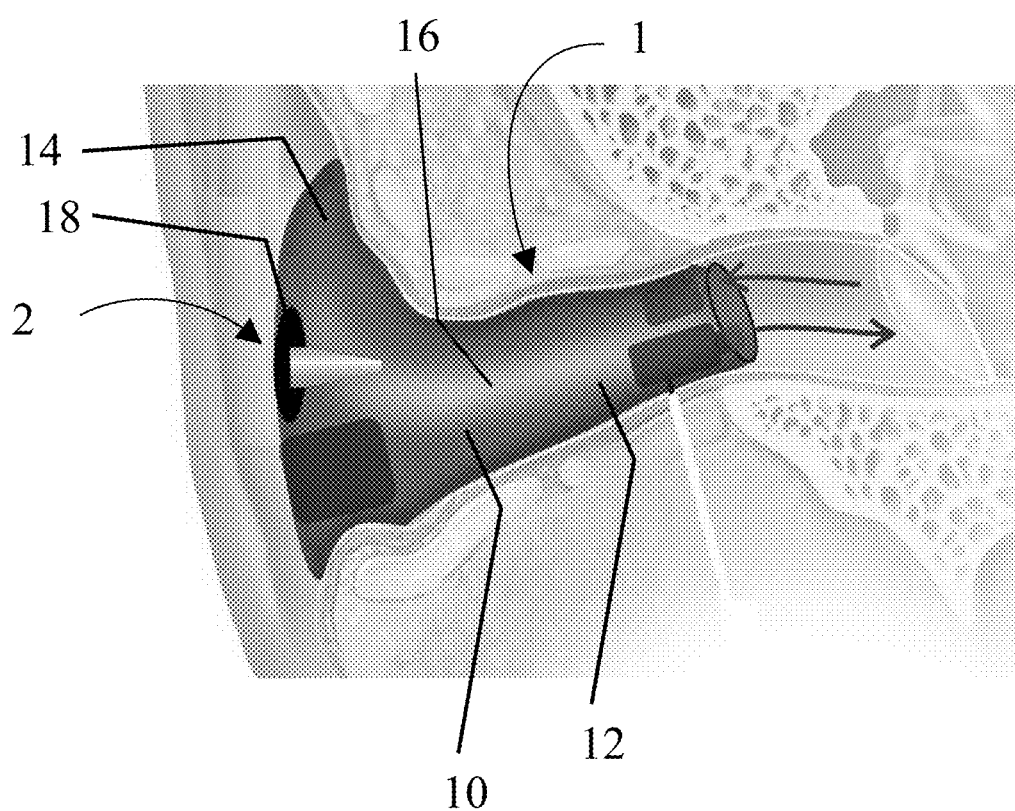
FIG. 1 is perspective cross-sectional view of a schematic representation of an earplug according to aspects of the present disclosure inserted in an ear canal.

Certain exemplary embodiments will now be described to provide an overall understanding of the principles of the structure, function, and use of the devices and methods disclosed herein. One or more examples of these embodiments are illustrated in accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such embodiments and variations are intended to be included within the scope of the present invention.

So that the present invention may more readily be understand, certain terms are first defined.

As used herein, the terms "about" or "approximately" or substantially" for any numerical values or ranges indicate a suitable dimensional tolerance that allows the part or collection of elements to function for its intended purpose as described herein. These terms indicate a ±10% variation about a central value.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time, or the subsequently described component may be at most about less than 10% of the total composition, in some embodiments, and in others, at most about less than 5%, and in still others at most about less than 1%.

The terms "first", "second", "third", etc. are used herein to describe various elements and these elements are not limited by these terms. These terms are used to distinguish one element form another. Thus, for example, a first element that is discussed herein could be termed a second element without departing of the teachings of the exemplary embodiments.

The terms "above", "below", "above", "left," "right," "in front," "behind," and the like are used herein to describe the spatial relationship of one or more elements from one or more other elements. The spatially relative terms are intended to encompass different orientations of the element in use or operations in addition to the orientations described herein and depicted in the figures.

The present application relates generally to devices, apparatus, systems and methods to regulate pressure in earplug. In some embodiments, the various devices and methods of the invention can be utilized to regulate pressure in various wired or wireless earpiece devices such as, for example and without any limitation, earplug, earbud, ear-tip, ear-pad, ear-flap, ear insert, earmuff, ear terminal, hearing aids, behind the hear device, headphones, earphones, other acoustic devices, or the like. In some embodiments, the earplug includes a body for sealing the ear canal and a pressure regulator (e.g. a valve) for equalizing pressure on either side of the regulator. In some embodiments, the pressure regulator is a passive device which automatically opens when there is a pressure differential.

In some embodiments, the earplug may further include, a communications system, including but not limited to one or more microphone, speaker, transmitter, receiver, or combination thereof. For example and without limitation, the earplug comprises at least one pressure regulator, at least one transmitting and receiving device for electrical or radio signal, at least one speaker, at least one transducer, at least one damper, or the like, or any combinations thereof. In some embodiments, the earpiece may also include, for example and without limitation, at least one housing, at least one acoustic seal, at least one support frame, at least one nozzle, at least one cable, at least one isolator, at least one connector, at least one transducer, at least one speaker, at least one diaphragm, at least one stopper, at least one magnet, at least one clamp, at least one clip, at least one frame, at least one cable, at least one acoustic tube, at least one vent, at least one screen, or the like, or any combinations thereof.

In the present application, processes, techniques, apparatus, and materials as known by one of ordinary skill in the art may not be discussed, described, or shown but are intended to be part of the enabling description where appropriate. For example, material fabrication and assembly may not be disclosed, nor attachment designs and procedures, but such, as known by one of ordinary skill in such arts, is intended to be included in the discussion herein when necessary. For example, if an earpiece includes a valve or an elongated fitting element and the design criteria is for the device to be inserted in the ear canal, then the material will have to have the properties necessary to maintain the earpiece within the ear canal (e.g., surface properties, bulk properties).

In the present application, some embodiments are directed to the use of a passive pressure valve that is closed when there is no differential pressure and opened when there is a pressure differential, wherein the open configuration is to allow the pressure to equalize between opposite sides of the valve. The passive pressure valve presents a number of advantages. For example, when coupled with an earpiece, the passive pressure valve allows for safe systems that can support high rates of pressure change without risk of barotrauma by the user. In another example, when coupled with an earplug, the passive pressure valve is better than a vented earplug. The passive pressure valve coupled with an earplug can regulate pressure while providing noise attenuation equivalent to a solid earplug by closing the sound transmission path with a closed valve. On the other hand, the 'vented' earplug, which regulates pressure via an open hole to vent the earplug, provides only low or no noise attenuation due to the open hole. By using a larger opening than in a traditional vented earplug, the passive valve coupled with an earplug has a reduced potential for clogging. The passive valve coupled with an earplug provides, in addition, a better platform for effective near-field magnetic induction (NFMI) communication, if desired, because sound can be produced more efficiently and with higher fidelity in a closed cavity; sound is produced with less efficiently and with lower fidelity in the open cavity from a vented earplug due to the presence of an open hole.

The noise attenuation from the passive pressure valve coupled with an earpiece can both protect hearing and provide for improved communication. For instance, the passive pressure valve can couple with not only an earplug but also with a microphone and a speaker that can be placed within or behind the earplug to transmit and receive communications. The system can be used with wireless communications, wired communications, music or other entertainment, hearing aids or other situational awareness systems that amplify or reduce outside noise through the use of a microphone outside the system and a speaker within the system.

Some embodiments are directed to the use of a pressure valve coupled with a noise reduction system, such as an earplug, for a dive helmet. Helmeted divers are exposed to high levels of noise such as noises that are self-generated (e.g. airflow through the demand-regulators during inhalation, bubble noise during exhalation) or noises that are transmitted through the helmet from underwater tools. For instance, noise levels inside a Mk-21 dive helmet can reach sustained levels over 100 dB(A) from either regulator operation or due to underwater tools (Wolgemuth et. al., 2008; Evans et. al., 2007). For effective communication, diver noise exposure in general should be limited to 84 dB(A) or less. In some embodiments the diver noise exposure can be limited via use of the devices disclosed herein to less than about 84 dB(A), about 80 dB(A), about 75 dB(A).

In such embodiments, the pressure valve coupled with an earplug (herein "pressure valve-earplug system") can provide hearing protection while maintaining easy and safe pressure equalization. A NFMI communication system can also be coupled with the pressure valve-earplug system to provide a clear, reliable communications without the use of batteries or electronics embedded in the earpiece. The communication can comprise, for example and without any limitation, at least one passive amplifier, at least one rare-earth magnet that function as both a receiver and a speaker, or the like, or a combination thereof.

In such embodiments, the pressure valve-earplug system can provide better noise attenuation and can be less susceptible to clogging than vented alternatives. The pressure valve-earplug system can function outside of an helmet (such as in a decompression chamber), and can be compatible with double protection. The pressure valve-earplug system is a stand-alone system that can require no changes to the helmet, which avoids requalification of the helmet and facilitates a fast transition between different applications, different application constraints, and different application requirements. The pressure valve-earplug system can be integrated with wireless communications, which can include near field magnetic induction technology to transmit audio without the need for a battery. The necessary transmitter coil can easily be attached to the helmet using the structure of a regular communication systems.

In some embodiments, the pressure valve-earplug system can achieve about about 25 dB to 79 dB average noise attenuation i.e. noise reduction. In some embodiments the noise attenuation achieved can be about 10 dB, about 15 dB, about 20 dB, about 25 dB, about 30 dB, about 35 db, about 40 dB, about 45 dB, about 50 dB, about 55 dB, about 60 db, about 75 dB, about 80 dB or any value or range of values between any of these values.

Alternatively, in some embodiments, the pressure valve-earplug system can reduce diver noise exposure to about 115 dB(A) to about 80 dB(A). Some embodiments reduce diver noise exposure to about 110 dB(A), about 100 dB(A), 95 dB(A), about 90 dB(A), 85 dB(A), about 84 dB(A), or reduce diver noise exposure to less than about 80 dB(A) or any value or range of values between any of these values. Reducing diver noise exposure increases the amount of time the diver can be exposed to the noise.

In some embodiments, the pressure valve-earplug system may not have pressure build-up when applying about 30 ft/min (0.25 psi/s) pressure rate to about 60 ft/min (0.5 psi/s) pressure rate. Alternatively, in some embodiments, the pressure valve-earplug system can have a working depth of about 500 ft., a working depth of about 550 ft., or a working depth off about 600 ft. In some instances a working depth of at least 600 feet can be achieved. In the case where pressure buildups in the ear, the diver can move their jaw to change the shape and size of the ear canal, creating an air path for pressure equalization.

Regarding the figures discussed below, similar reference numbers and letters refer to similar items in different figures, and, therefore, once an item is defined in one figure, it may not be discussed or redefined in another figure.

Various embodiments disclosed herein are configured for use as a pressure regulator within an earpiece, such as a pressure regulator 2 within an earplug 1 as illustrated in FIG. 1. The earplug 1 may employ any earplug body type including but not limited to single, dual or triple flanged elastomer earplug, foam earplug, silicon earplug, or the like, or any combinations thereof. In some embodiments, the earplug 1 comprises, for example and without any limitation, a flexible or rigid body 10 having a substantially conically shaped insert end 12 configured to be inserted into an ear canal and an enlarged flange end 14 opposite the insert end configured to block an opening of the ear canal. The body 10 may further include conduit 16 traversing the insert end 12 and enlarged flange end 14 that allows access to the ear canal. In some embodiments, the earplug 1 comprises a pressure regulator 2 comprising a valve assembly 18 designed to provide access to the conduit through the enlarged flange end 14. The pressure regulator 2 can be incorporated into the enlarged flange end 14 or elsewhere along the conduit of the earplug 1.

Figure 2A:
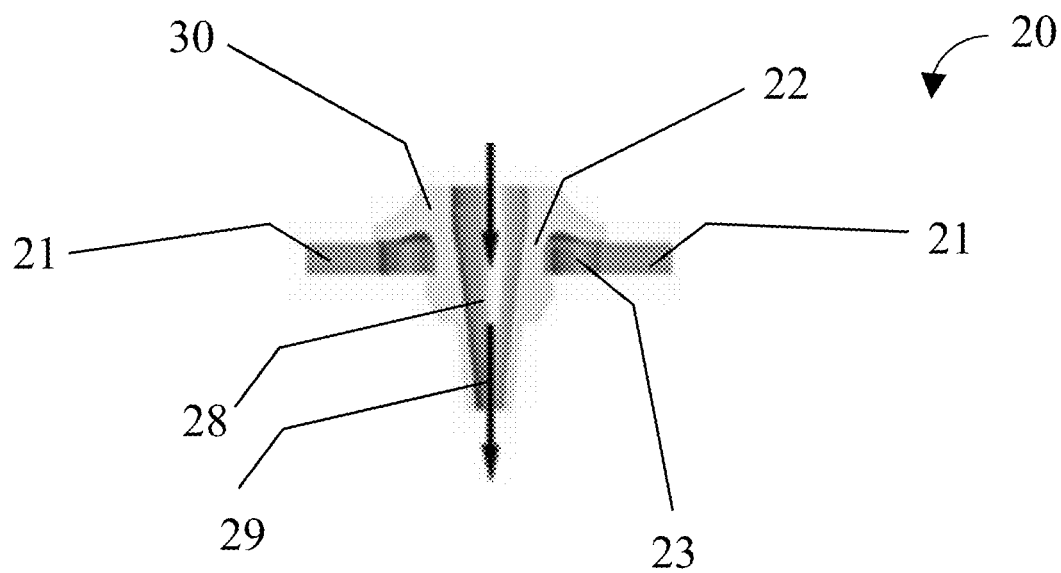
FIG. 2A is a cross-sectional side view of a schematic representation of an umbrella valve shown with higher external pressure according to aspects of the present disclosure.
Figure 2B:
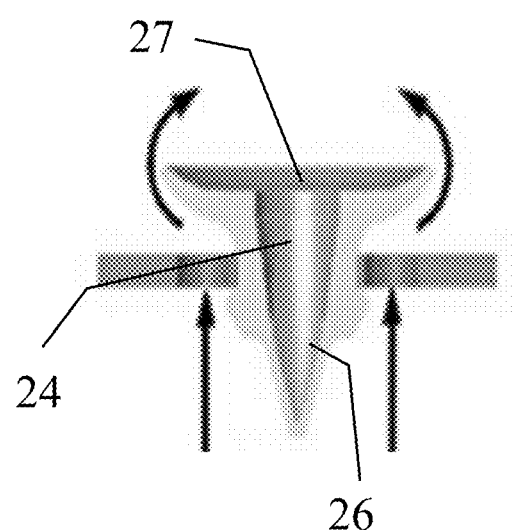
FIG. 2B is a side view of a schematic representation of an umbrella valve shown with higher external pressure according to aspects of the present disclosure.

Embodiments of the invention includes a valve assembly 20 that is described in detail in FIGS. 2A-B. The valve assembly 20 may be a passive valve assembly that opens automatically when sufficient pressure differential is present. The valve assembly 20 has a flange 21, a primary orifice 22 on the flange end, one or more secondary orifices 23 surrounding the primary orifice 22 on the flange end, and a valve body 24 disposed within the flange end. The valve body 24 has a conically shaped body 26 and an umbrella 27 disposed on an proximal end of the conically shaped body. A valve conduit 28 is located within the conically shaped body 26 and has an opening on the umbrella and a reversibly sealable opening 29 located at the opposite end of the umbrella 27 opening, more specifically at the distal end of the conically shaped body 26. The umbrella 27 of the valve body 24 has the size to cover one or more primary orifices 22, one or more secondary orifices 23, or one or more primary orifices 22 and one or more secondary orifice 23. The valve body 24 may be attached with the flange end using, for example, sealant material 30.

The umbrella 27 covers one or more secondary orifices 23 resulting in a close valve as illustrated in FIG. 2A. The valve conduit 28 from the outside is blocked when the pressure outside is equal to the pressure inside the ear. Those familiar with the art would appreciate that the closed valve results in sound attenuation similar to unvented earplugs. However, if a pressure differential exists between the inside and outside of the earplug the pressure will force the reversibly sealable opening to open, allowing air to pass through the valve conduit, in or out, equalizing the pressure within the ear as illustrated in FIG. 2B. When the inner pressure builds up, the umbrella 27 extends axially upward allowing air to pass through one or more secondary orifices.

Embodiments of the invention are not limited to a particular valve assembly such as the valve assembly 20 described above. Alternatively, the valve assembly can be, for example and without limitation, a duckbill valve assembly, a belleville valve assembly, a valveball assembly, a cross-split valve assembly, a dome valve assembly, or the like, or any combinations thereof. In some embodiments, the valve assembly comprises any of silicon, fluorosilicone, fluoro elastomer, perfluoroelastomer, nitrile, ethylene propylene, natural rubber, butyl, polyisoprene, or the like, or any combinations thereof.

Figure 3A:
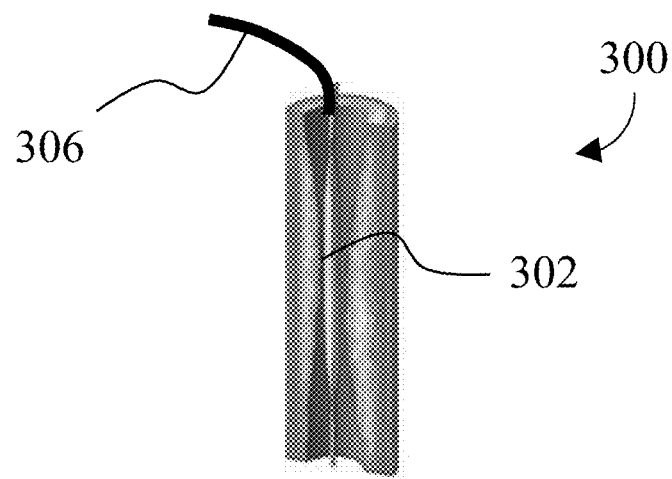
FIG. 3A is a cross section view of a schematic representation of a tube with a deflated balloon according to some embodiments disclosed herein.
Figure 3B:
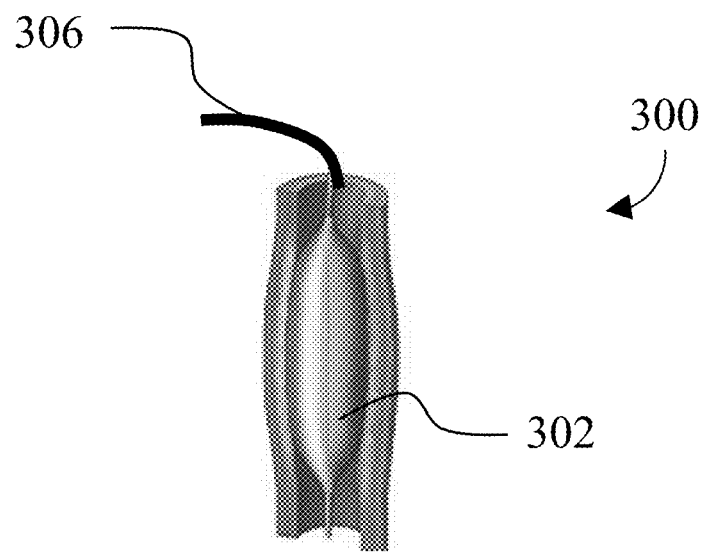
FIG. 3B is a cross section view of a schematic representation of a tube with an inflated balloon according to some embodiments disclosed herein.
Figure 3C:
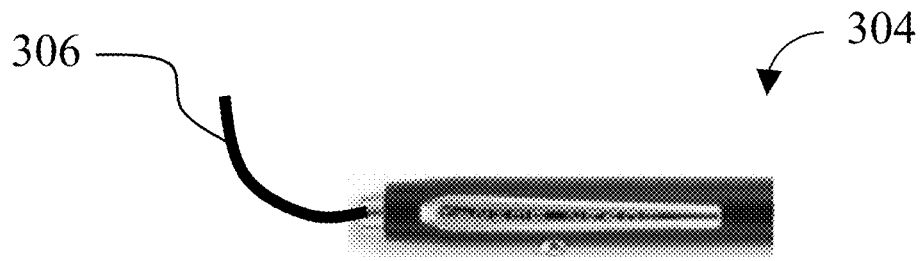
FIG. 3C is a cross section view of schematic representation of a control valve for an balloon according to aspects of the present invention.

Instead of being automatically actuated like in the valve assembly 20, a valve could be user actuated to allow pressure equalization or to achieve reduced sound attenuation to facilitate communication or situational awareness. One possible embodiment of a user actuated valve is an inflatable structure 300 as illustrated in FIG. 3A-C, that is inserted in an earplug conduit or simply directly in the ear canal. The inflatable structure 300 can include an angioplasty balloon 302 that could be inflated and deflated independently in each ear as shown by FIG. 3A and FIG. 3B respectively. The angioplasty balloon 302 can be controlled by means of a mechanism 304 as illustrated in FIG. 3C. The mechanism 304 can be connected to the angioplasty balloon 302 by tubing 306 and could push air into the balloons in both ears when actuated. One such mechanism is a push button plunger/piston similar to a ballpoint pen mechanism When the plunger is depressed air is pushed into the balloon(s), when a second button is depressed the plunger is released drawing air out of the balloon(s). The valve could also be an electronic system automatically actuated by sound or pressure levels or other actuation signal.

Figure 4A:
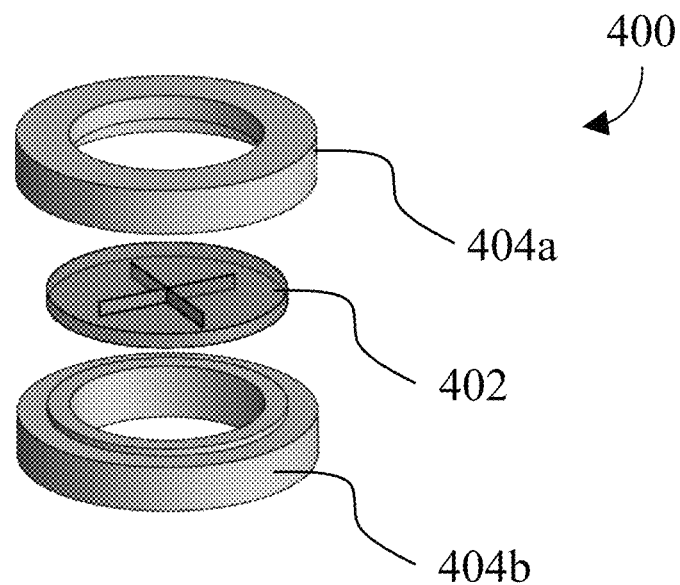
FIG. 4A is an exploded view of a schematic representation of a two-way diaphragm elastomer valve for use in some embodiments of the earplug disclosed herein.
Figures 4B, 4C:
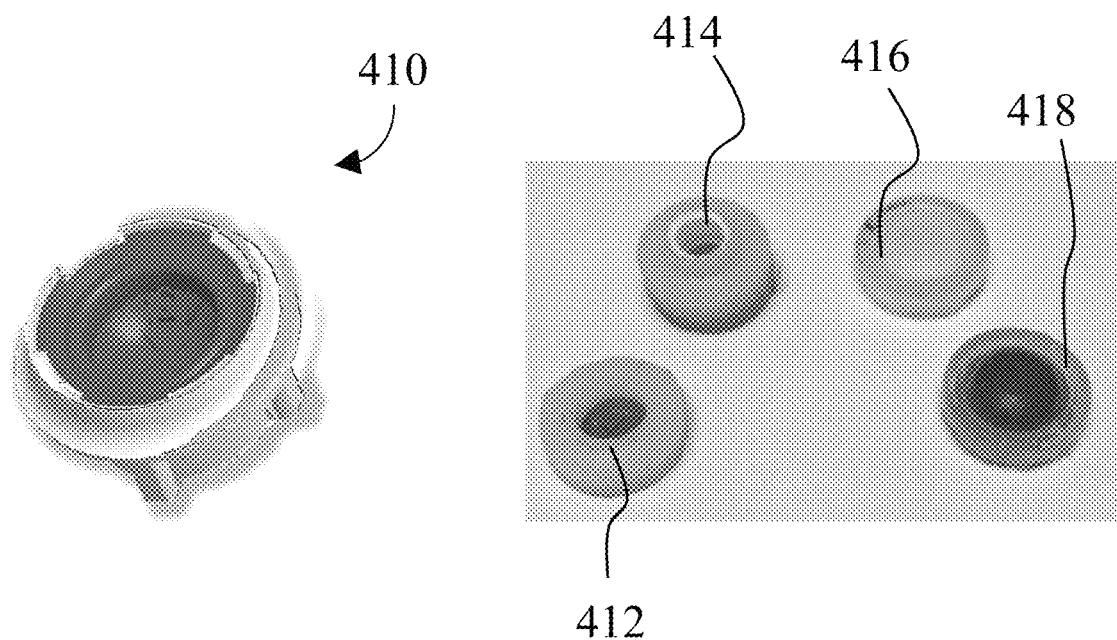
FIG. 4B is a perspective view of a schematic representation of a two-way diaphragm elastomer valve for use in some embodiments of the earplug disclosed herein.
FIG. 4C is a perspective view of two-way diaphragm elastomer valves for use in some embodiments of the earplug disclosed herein.

FIGS. 4A-C schematically depict valves according to different embodiments of the present invention. In some embodiments, a valve 402 can be fit within an assembly 400 that allows the valve 402 to pop-out in the unlikely event of high pressure build up on either sides of the valve. The valve assembly 400 comprises two rigid snap fit parts 404a and 404b that snugly enclose the valve 402 as illustrated in FIG. 4A. The rigid valve assembly can be press fit, for example, into a precise bore in an outer end of an earplug. The valve 402 is pushed inwards out of its housing, allowing large air paths through the assembly to equalize pressure, when the pressure outside the ear exceeds the pressure inside the ear by about 0.1 psi, or when the pressure outside the ear exceeds the pressure inside the ear by about 0.3 psi, or when the pressure outside the ear exceeds the pressure inside the ear by about 0.5 psi. The whole valve assembly will pop out of the earplug allowing pressure equalization when the pressure inside the ear exceeds the pressure outside the ear by by about 5 psi for safety. In the event of valve damage, the whole assembly can be replaced without replacing the custom earplugs. FIG. 4B schematically depicts another valve assembly 410 according to certain embodiments, and FIG. 4C depicts split diaphragm valves 412, 414, 416, and 418, wherein valves 412, 414, 416, and 418 have different diameters.

Two important parameters of a functioning valve are the opening pressure and the seal upon closing. The largest contributing factor to a decrease in attenuation in a poorly fitting earplug is air path leaks through the seal and plug. Accordingly, a valve must be able to handle repeated activation without becoming warped. For this reason, in certain embodiments of the present invention, a two way cross-split valve assembly, also known as an elastomer split diaphragm, or "x-fragm", is used for incorporation into pressure regulator systems.

In the present application, the valve from different embodiments can be designed to open at low or high pressures and can be used in a wide range of application such as, for example, in earpiece devices, medical devices food dispensing devices, or the like. In some embodiments, the valve can be designed to be functional for a high number of cycles without warping and for opening pressure of about 0.3 psi, or for opening pressure of about 0.5 psi, or for opening pressure of about 0.7 psi, or for opening pressure of about 0.9 psi, or for opening pressure of about 1.0 psi, or for opening pressure of about 1.1 psi, or for opening pressure of about 1.3 psi, or or for opening pressure of about 1.5 psi. In some embodiments, the valve can be made of a circular piece of material with a thickness in a range of about 0.5 mm to about 5 mm, or a thickness in a range of about 0.5 mm to about 4 mm, or a thickness in a range of about 0.5 mm to about 3 mm, or a thickness in a range of about 0.5 mm to about 2 mm, or a thickness in a range of about 0.5 mm to about 1 mm. In some embodiments, the valve can be made of a circular piece of material with a thickness of about 0.6 mm, or a thickness of about 0.8 mm, or a thickness of about 1.0 mm. In some embodiments, the valve can be made of a circular piece of material with a diameter in a range of about 4 mm to about 20 mm, or with a diameter in a range of about 4 mm to about 15 mm, or with a diameter in a range of about 4 mm to about 10 mm, or with a diameter in a range of about 4 mm to about 8 mm. In some embodiments, the valve can be made of a circular piece of material with a diameter of about 4 mm, or with a diameter of about 6 mm, or with a diameter of about 8 mm, or with a diameter of about 10 mm.

Figure 5A:
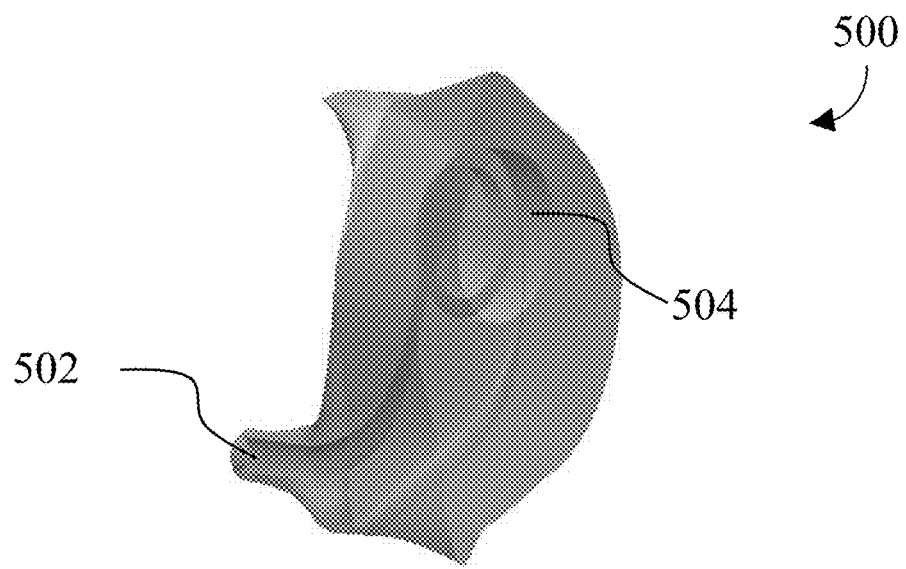
FIG. 5A is a perspective view of a schematic representation of a retention ring according to aspects of the present disclosure.
Figure 5B:
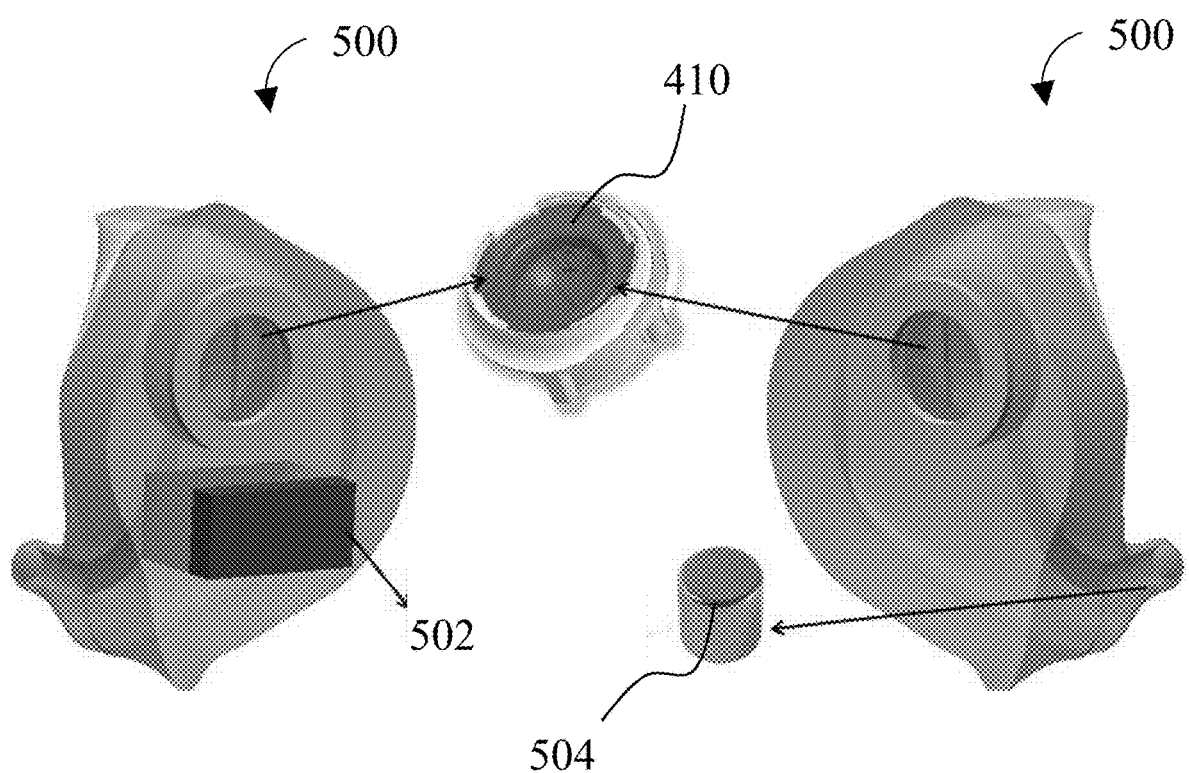
FIG. 5B is a perspective view of a schematic representation of a left and a right retention rings according to aspects of the present disclosure.

FIGS. 5A-B schematically depict a pressure equalizing earpiece 500, according to some embodiments of the invention, that can integrate communications. The pressure equalizing earpiece 500 can be used to reduce the noise levels exposed to helmeted divers and can combine earplug and valve, which are closed except during pressure equalization.

The pressure equalizing earpiece 500 can be made of a custom molded silicone earpiece comprising at least one vent 502 and at least one circular bore 504 as illustrated in FIG. 5A. In some embodiments, the vent 502 can have a cross section in a range of about 1 mm to about 10 mm, or a cross section in a range of about 2 mm to about 8 mm, a cross section in a range of about 2 mm to about 6 mm, or a cross section in a range of about 2 mm to about 4 mm. In some embodiments, the vent 502 can have a cross section of about 1 mm, or a cross section of about 2 mm, a cross section of about 4 mm, or a cross section of about 6 mm, or a cross section of about 8 mm, or a cross section of about 10 mm. In some embodiments, the circular bore 504 can have a cross section in a range of about 5 mm to about 20 mm, or a cross section in a range of about 5 mm to about 15 mm, or a cross section in a range of about 5 mm to about 10 mm, or a cross section in a range of about 8mm to about 10 mm. In some embodiments, the circular bore 504 can have a cross section of about 5 mm, or a cross section of about 8 mm, or a cross section of about 10 mm, or a cross section of about 15 mm. The bore can provide a press-fit for a valve, which can be installed on the outside of the earplug.

Valve assembly 410, as illustrated in FIG. 5B, is an exemplary valve that can be combined with the pressure equalizing earpiece 500. Still referring to FIG. 5B, the pressure equalizing earpiece 500 can also be combined with at least one passive near field magnetic induction (NFMI) receiver 502 that can receive wireless audio signals from a transmitter, at least one passive amplifier, at least one rare-earth magnet 504 that acts as both a receiver and speaker, or the like, or any combinations thereof.

Figure 6:
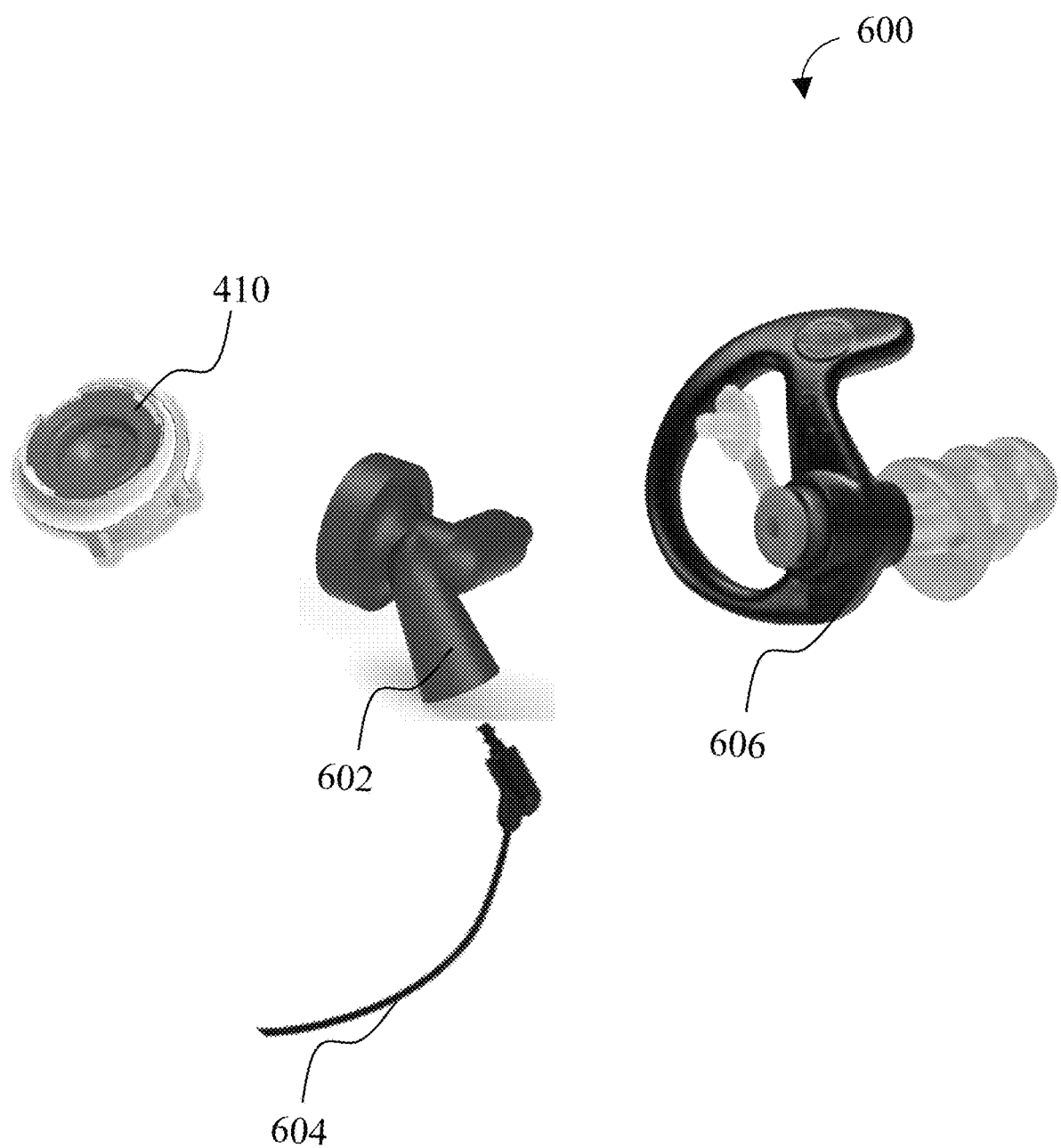
FIG. 6 is a perspective view of a disassembled earplug according to aspects of the present invention.

FIG. 6 depicts another pressure equalizing earpiece 600 according to some embodiments of the invention. The pressure equalizing earpiece 600 comprises a valve 400, an adapter 602, a connection cable 604, and a flanged earplug 606.

Figures 7A, 7B:
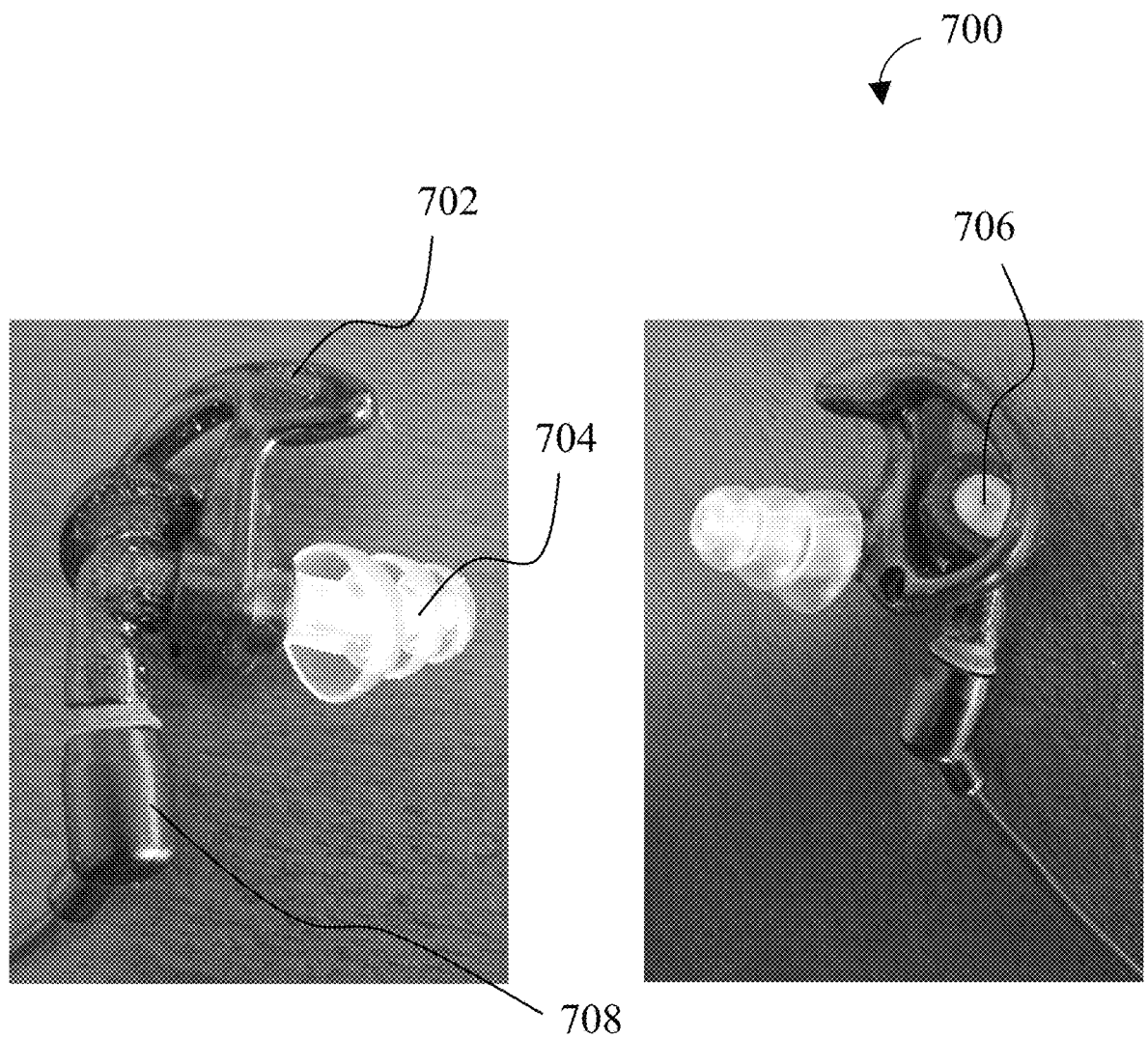
FIG. 7A is a perspective view of an assembled left-side earplug according to some embodiments disclosed herein.
FIG. 7B is a perspective view an assembled right-side earplug according to some embodiments disclosed herein.

FIGS. 7A-B depict another pressure equalizing earpiece 700 according to some embodiments of the invention. FIG. 7A shows a top view of the equalizing earpiece 700 and FIG. 7B shows a bottom view of the equalizing earpiece 700. The pressure equalizing earpiece 700 comprises, for instant, a retention ring 702, a triple flanged earplug 704, a two-way valve 706, and a communication transducer 708.

Figure 8:
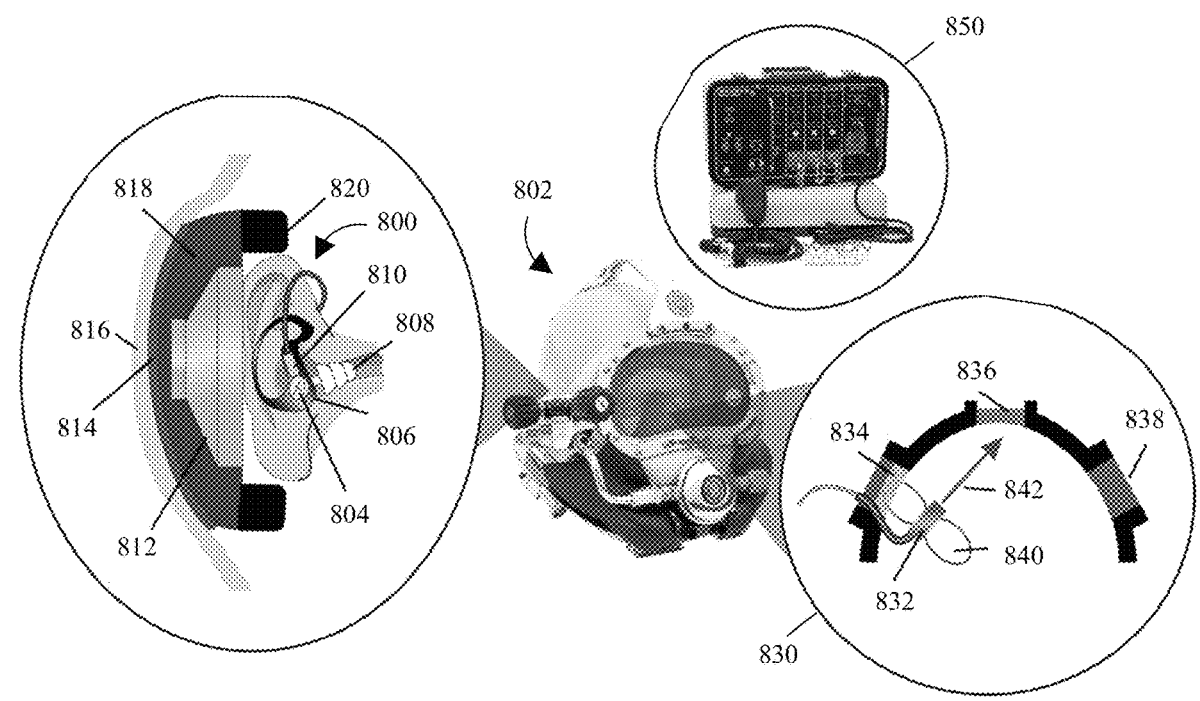
FIG. 8 is a schematic representation of a system incorporating an earplug, a divers helmet, and communications system in accordance with some embodiments disclosed herein.

In some embodiments, a pressure equalization piece 800 can be coupled with a dive helmet 802 as illustrated in FIG. 8. The pressure equalization piece 800 can include, for example and without any limitation, at least one valve 804, at least one retention ring 806, at least one flange 808, at least one speaker 810, or the like, or any combinations thereof. The pressure equalization piece 800 can couple with the helmet 802 using, for example and without any limitation, at least one backup speaker 812, at least one foam backing 814, an helmet cover 816, at least one plastic adaptor 818, at least one foam earcup 820, or the like, or any combinations thereof. The helmet 802 can also be coupled, for example and without any limitation, with at least one microphone system 830, at least one digital signal processing (DSP) system 850, or the like, or a combination thereof. The microphone system 830 can include, for example and without any limitation, at least one directional microphone 832, noise absorbing material 834, at least one port 836 such as a port to regulator, at least one valve 838 such as a one-way valve, at least one front lobe 840, or the like, or any combinations thereof. In certain embodiments, the directional microphone 832 is null toward 842 the regulator 836.

Figure 9:
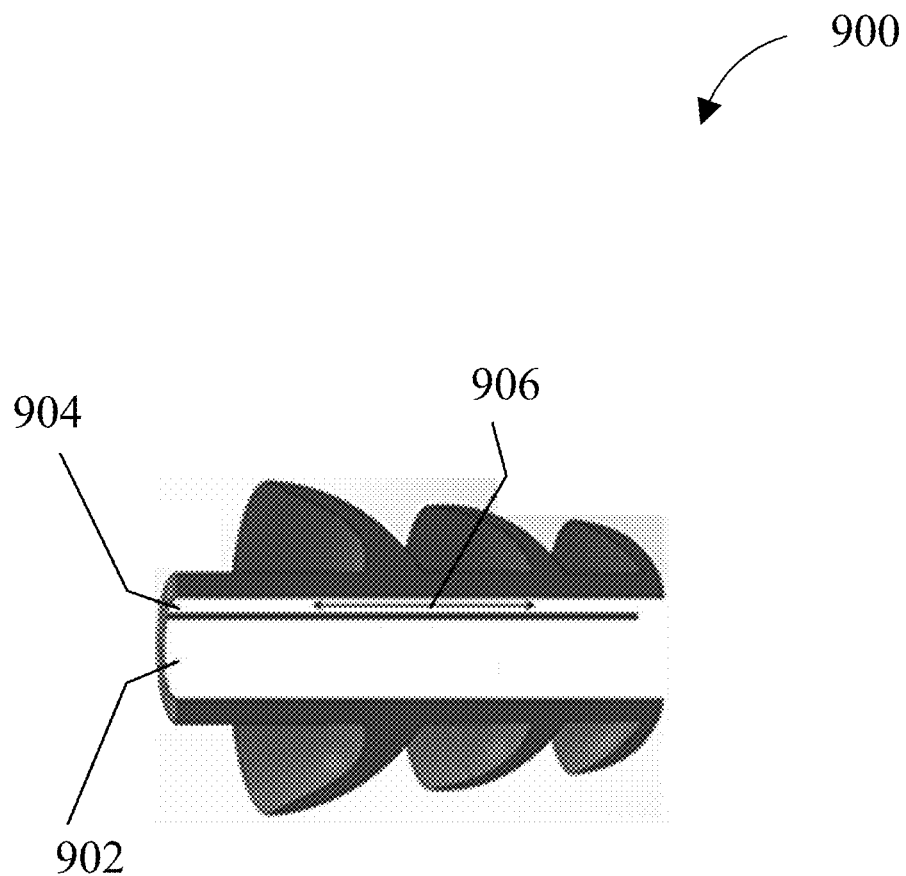
FIG. 9 is a cross-sectional view of a schematic representation of a multichannel earplug according to aspects of the present invention.

FIG. 9 depicts a cross-sectional view of a schematic representation of an earplug 900 according to some embodiments of the invention. Some embodiments further comprise at least one additional to house additional components. The additional components are selected from electrical components, communications system components, wiring and the like, or combinations thereof. In some embodiments, the at least one additional conduit is sealed against the external atmosphere. In some embodiments the external environment is water, and the additional conduit is sealed against water influx. Referring to the figure again, the earplug 900 comprises, for example and without any limitation, a first conduit 902 and a second conduit 904, wherein the first conduit 902 is a pressure equilibrium conduit and the second conduit 904 is an acoustic conduit. The pressure equilibrium channel is designed to couple with a pressure valve (not shown here) such that the pressure between the inside and the outside of the ear is equilibrated. The acoustic channel is designed to connect at least one transducer (not shown here) to an eardrum (not shown here) and to transmit and receive sounds. In certain embodiments, the acoustic channel is coupled with a close flexible structure that prevent water to penetrate into the eardrum or into the path between the at least one transducer and the eardrum.

What is claimed:
1. A pressure-regulating earplug comprising:
   an earplug body having an external surface adapted for sealingly engaging an ear canal, the earplug body comprising a conduit configured to provide fluid communication with an external atmosphere and the ear canal; and
   a pressure regulator affixed to the earplug body in-line with the conduit, configured to be normally closed, preventing fluid communication between the external atmosphere and the ear canal, and selectively open, comprises:
   a first normally-closed passive valve configured to automatically open, permitting fluid communication between the external atmosphere and the ear canal, when pressure within the ear canal exceeds pressure within the external atmosphere by a first opening threshold; and
a second normally-closed passive valve disposed substantially concentric to the first passive valve and configured to automatically open, permitting fluid communication between the external atmosphere and the ear canal, when the pressure within the external atmosphere exceeds the pressure within the ear canal by a second opening threshold; and
wherein:
the first and second normally-closed passive valves form a valve assembly that comprises:
a conically shaped body; and
a valve conduit located within the conically shaped body having an opening on a first side of the conically shaped body and a reversibly sealable opening on a second side of the conically shaped body; and
at least an orifice parallel with the valve conduit; and
an umbrella around the opening on the first side of the valve conduit and configured to reversibly seal the at least an orifice.

2. The pressure-regulating earplug of claim 1, wherein the earplug body comprises a flanged earplug.

3. The pressure-regulating earplug of claim 2, wherein the flanged earplug is a single, a dual or triple flanged earplug.

4. The pressure-regulating earplug of claim 2, wherein the earplug is an elastomer earplug, foam earplug, silicon earplug, or any combination thereof.

5. The pressure-regulating earplug of claim 1, wherein the pressure regulator opening threshold is at a pressure differential of about 0.1 psi or higher to allow pressure to flow high to low.

6. The pressure-regulating earplug of claim 1, wherein the pressure regulator opening threshold is a pressure differential of less than about 0.5 to allow pressure to flow from high to low.

7. The pressure-regulating earplug of claim 1, wherein the pressure regulator opening threshold is a pressure differential from about 0.1 psi to about 1.5 psi.

8. The pressure-regulating earplug of claim 1, wherein the pressure regulator comprises any of silicon, fluorosilicone, fluoro elastomer, perfluoroelastomer, nitrile, ethylene propylene, natural rubber, butyl, polyisoprene, or any combination thereof.

9. The pressure-regulating earplug of claim 1 further comprising a communication system.

10. The pressure-regulating earplug of claim 1, wherein the pressure-regulator is incorporated along the conduit.

11. The pressure-regulating earplug of claim 1, wherein the valve assembly of the pressure regulator is designed to provide access to the conduit through the external surface.

12. The pressure-regulating earplug of claim 1, wherein the earplug is adapted to seal the ear canal when the valve assembly is closed.

13. A pressure-regulating earplug comprising:
an earplug body having an external surface adapted for sealingly engaging an ear canal, the earplug body comprising a conduit configured to provide fluid communication with an external atmosphere and the ear canal, and further comprising at least one additional conduit; and
a pressure regulator affixed to the earplug body in-line with the conduit, configured to be normally closed, preventing fluid communication between the external atmosphere and the ear canal, and selectively open, wherein the pressure regulator comprises:
a first normally-closed passive valve configured to automatically open, permitting fluid communication between the external atmosphere and the ear canal, when pressure within the ear canal exceeds pressure within the external atmosphere by a first opening threshold; and
a second normally-closed passive valve disposed substantially concentric to the first passive valve and configured to automatically open, permitting fluid communication between the external atmosphere and the ear canal, when the pressure within the external atmosphere exceeds the pressure within the ear canal by a second opening threshold; and
wherein the at least one additional conduit is configured to house additional components; and wherein:
the first and second normally-closed passive valves form a valve assembly that comprises:
a conically shaped body; and
a valve conduit located within the conically shaped body having an opening on a first side of the conically shaped body and a reversibly sealable opening on a second side of the conically shaped body; and
at least an orifice parallel with the valve conduit; and
an umbrella around the opening on the first side of the valve conduit and configured to reversibly seal the at least an orifice.

14. The pressure-regulating earplug of claim 13, wherein the at least one additional conduit is sealed against the external atmosphere.

15. The pressure-regulating earplug of claim 14, wherein the external atmosphere is water, and the additional conduit is sealed against water influx.

16. The pressure-regulating earplug of claim 13, wherein the additional components are selected from electrical components, communications system components, wiring, or combinations thereof.

17. A pressure-regulating earplug system comprising:
a diver's helmet configured to seal an external atmosphere within the diver's helmet from water outside of the diver's helmet, wherein the diver's helmet comprises:
a backup speaker configured to be disposed proximal a diver's ear; and
an earcup configured to be disposed about the diver's ear; and
a pressure-regulating earplug comprising:
an earplug body having an external surface adapted for sealingly engaging an ear canal, the earplug body comprising a conduit configured to provide fluid communication with the external atmosphere and the ear canal; and
a pressure regulator affixed to the earplug body in-line with the conduit, configured to be normally closed, preventing fluid communication between the external atmosphere and the ear canal, and selectively opening, comprises:
a first normally-closed passive valve configured to automatically open, permitting fluid communication between the external atmosphere and the ear canal, when pressure within the ear canal exceeds pressure within the external atmosphere by a first opening threshold; and
a second normally-closed passive valve disposed substantially concentric to the first passive valve and configured to automatically open, permitting fluid communication between the external atmosphere and the ear canal, when the pressure within the external atmosphere exceeds the pressure within the ear canal by a second opening threshold; and wherein:

the first and second normally-closed passive valves form a valve assembly that comprises:

a conically shaped body; and a valve conduit located within the conically shaped body having an opening on a first side of the conically shaped body and a reversibly sealable opening on a second side of the conically shaped body; and at least an orifice parallel with the valve conduit; and an umbrella around the opening on the first side of the valve conduit and configured to reversibly seal the at least an orifice.

* * * * *